(12) United States Patent
Hanko et al.

(10) Patent No.: US 9,146,138 B2
(45) Date of Patent: Sep. 29, 2015

(54) PROBE ARRANGEMENT

(75) Inventors: Michael Hanko, Dresden (DE); René Kündscher, Radeburg (DE); Torsten Pechstein, Radebeul (DE)

(73) Assignee: Endress + Hauser Conducta Gesellschaft für Mess- und Regeltechnik mbH + Co. KG, Gerlingen (DE)

( * ) Notice: Subject to any disclaimer, the term of this patent is extended or adjusted under 35 U.S.C. 154(b) by 980 days.

(21) Appl. No.: 13/109,065

(22) Filed: May 17, 2011

(65) Prior Publication Data

US 2011/0290045 A1    Dec. 1, 2011

(30) Foreign Application Priority Data

May 17, 2010    (DE) .......................... 10 2010 029 029

(51) Int. Cl.
  *G01D 11/24*    (2006.01)
  *G01N 27/333*    (2006.01)

(52) U.S. Cl.
  CPC ............ *G01D 11/245* (2013.01); *G01N 27/333* (2013.01)

(58) Field of Classification Search
  CPC .................................................. G01D 11/245
  USPC ........................................................ 73/866.5
  See application file for complete search history.

(56) References Cited

U.S. PATENT DOCUMENTS 7,272,983 B2 *   9/2007  Caderas ...................... 73/866.5
7,806,009 B2    10/2010  Tottewitz

FOREIGN PATENT DOCUMENTS

| CN | 1681609 A | 10/2005 |
|----|-----------|---------|
| CN | 1912402 A | 2/2007 |
| CN | 101093209 A | 12/2007 |
| DE | 8633674.6 | 4/1987 |
| DE | 10241833 A1 | 3/2004 |
| DE | 202006007648 U1 | 8/2006 |
| DE | 102006022981 A1 | 11/2007 |
| DE | 102007030584 A1 | 1/2009 |
| EP | 1887348 A1 | 2/2008 |

\* cited by examiner

*Primary Examiner* — Paul West
(74) *Attorney, Agent, or Firm* — Bacon & Thomas, PLLC

(57) ABSTRACT

A probe arrangement, in the case of which a probe is arranged within a tubular housing, wherein the tubular housing has at least one process window open to the process medium, and at least one functional element is secured on the probe and surrounded by the process medium. In order to suppress a taking along of the process medium during transfer of the functional element from the measured medium into a rinsing chamber, the tubular housing includes at least one treatment window open opposite the probe (3), preferably for washing, rinsing and/or calibrating the functional element, wherein the functional element is movable between the process window and the treatment window, and, during the measuring in the process medium, the at least one functional element is arranged approximately coincident with the at least one process window of the housing.

12 Claims, 7 Drawing Sheets

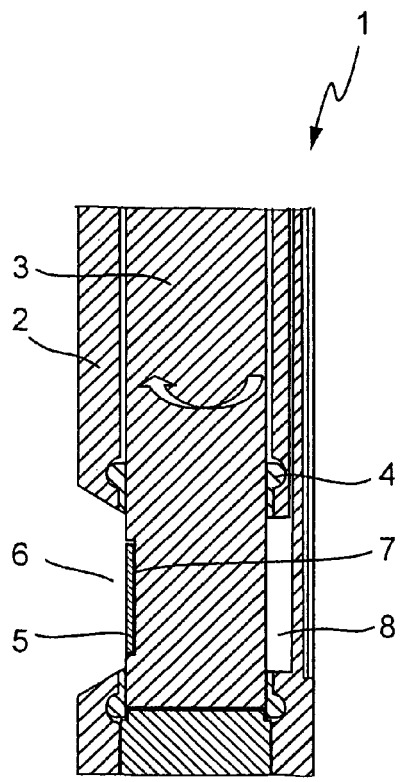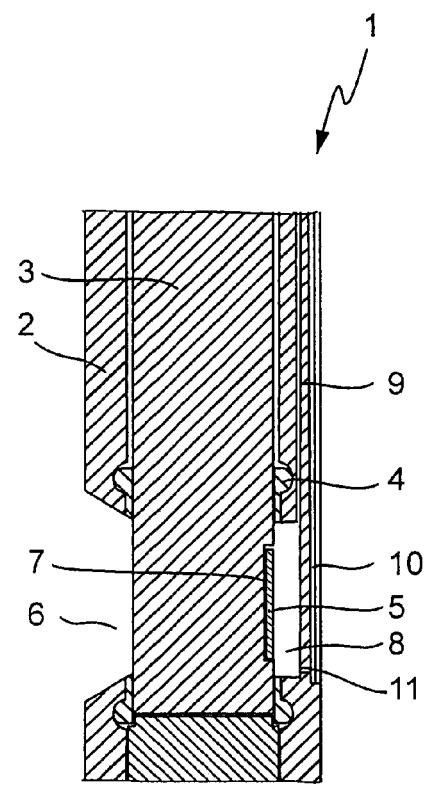
Fig. 2a
Fig. 2c
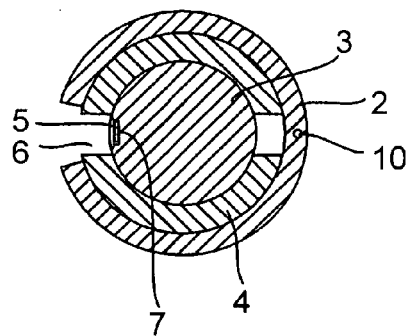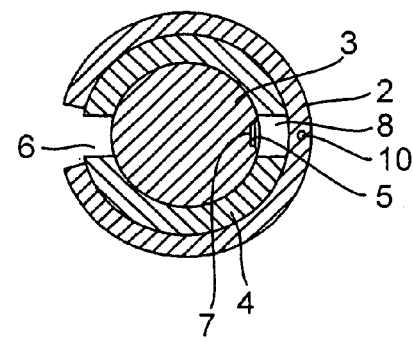
Fig. 2b
Fig. 2d

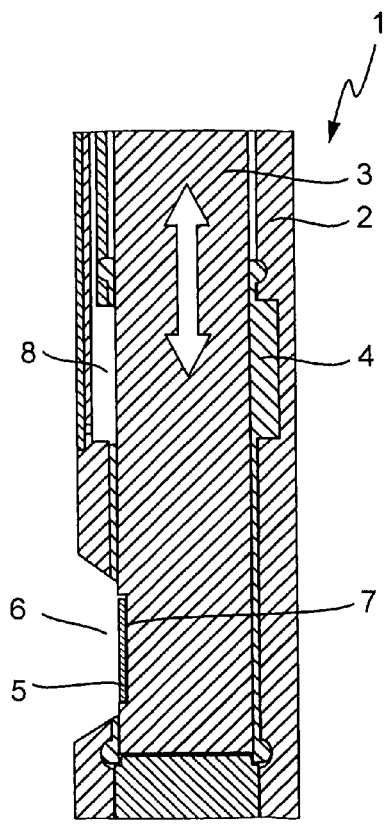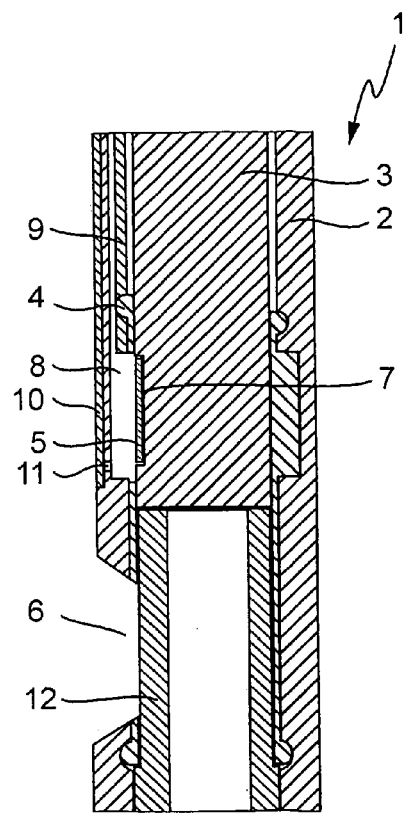
Fig. 3a  Fig. 3c
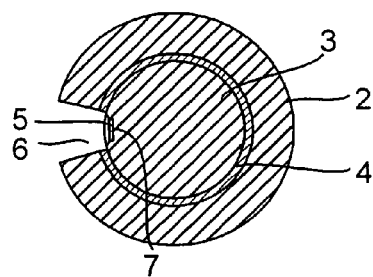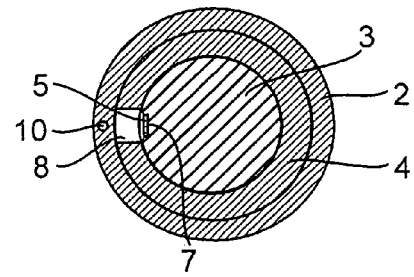
Fig. 3b  Fig. 3d

PROBE ARRANGEMENT

TECHNICAL FIELD

The invention relates to a probe arrangement, in the case of which a probe is arranged within a tubular housing, wherein the tubular housing has a traversing window open to the process medium, and secured on the probe is a functional element, which is surrounded by the process medium.

BACKGROUND DISCUSSION

For measuring various process variables in liquid media, sensor arrangements are usually used, which are immersed in the liquid medium. Such sensor arrangements are, as is presented in FIG. 1, preferably composed of a double-walled tubular housing 2 and a long, extended sensor 3 made from glass, synthetic material or metal, which is arranged within the tubular housing 2 and on whose tip a sensitive element 5 is secured. In such case, the tubular housing 2 extends over the sensitive element, 5 and is sealed below by the sensitive element 5. The tubular housing 2 is generally referred to as an immersion tube, since an end of this immersion tube is in contact with the process medium. Through two traversing, oppositely positioned openings 6 on the end of the immersion tube extending into the measured medium, the process medium enters into the interior of the immersion tube, and comes there in contact with the sensitive element 5.

In order to clean or to recalibrate the sensitive element, the entire sensor arrangement with the immersion tube and the sensor body is translated out of the process medium and into a rinsing chamber. In such case, a large amount of process medium is brought along and into the rinsing chamber, which leads to contamination, and especially always proves disadvantageous, whenever the sensitive element should be newly calibrated, since, in this case, the rinsing chamber must first be cleaned of the process medium using a large amount of washing or rinsing medium before a calibration medium can be introduced.

SUMMARY OF THE INVENTION

An object of the invention is thus to provide a sensor arrangement, in the case of which a taking along of the process medium during the transfer of the sensitive element from the measured medium into a rinsing chamber is largely suppressed.

According to the invention, the object is achieved by the features that the tubular housing has at least one treatment window lying opposite the probe, preferably for rinsing and/or calibrating the functional element, wherein the functional element is movable between the process window and the treatment window, and, during measuring in the process medium, the at least one functional element is arranged approximately coincident with the at least one process window of the housing. In this way, the rinsing and/or calibration procedure is performed in the probe arrangement itself. A cumbersome withdrawal of the probe arrangement from the process medium, in order to perform a rinsing and/or calibration procedure, can thus be omitted, as can likewise the providing of a rinsing chamber. Through the exact-fitting dimensions between the functional element and the process window or the treatment window, in the case of a swinging of the functional element from a measuring position to a rinsing or calibration position, essentially no process medium is carried along, whereby a contamination of the probe arrangement is largely suppressed. This has the result that, before a calibration procedure, the method step of rinsing the functional element can be reduced to a minimum consumption of time and washing agent.

The term "probe" in the following means a sensor with a sensitive area, a treatment probe with an active, or activatable, area or a sampling probe having an opening for accommodating a sample. The sensor is, for example, a pH sensor for determining pH value in a medium. In the case of a treatment probe, an electrode, for example, is provided for introducing an electrical current into in a medium. The sensitive area, the active, or activatable, area and the electrode are generically referred to with the term "functional element".

The term "process medium" means herein the medium which, with the assistance of the probe installed in the probe arrangement, is analyzed, or which, with the assistance of the probe, is treated in some manner, be it through the addition of an electrical current or through the removal of a sample by means of the probe.

Advantageously, the at least one functional element lies on the probe. Thus, mechanically stable functional elements can be placed on the probe very easily, e.g. via adhesive, whereby the manufacture of the probe arrangement is greatly simplified. A dead volume in the probe arrangement, into which the process medium can penetrate, can, in the case of this embodiment, be largely eliminated, so that a contamination of the probe arrangement by process medium is almost completely absent.

Alternatively, the at least one functional element is arranged in a cavity of the probe. The dimensions of the cavity are selected in such a manner, that the functional element does not protrude out from the cavity. This embodiment is especially suitable for mechanically sensitive functional elements, wherein dead volume for the penetration of process medium to be examined is kept very small.

In an embodiment, the functional element is arranged laterally on the probe, opposite the lengthwise extent of the tubular housing. An advantage here lies in the fact that, through the covering of the process window with the functional element, the dead volume into which process medium can penetrate, is kept very small, since the process window and the functional element have almost the same dimensions and a good seal exists between these. Through this structural measure, only a small amount of process medium can penetrate into the probe arrangement.

In a further development, the at least one treatment window is advantageously arranged opposite the process window at an approximately equal height, wherein the probe is mounted rotatably, whereby the functional element is rotatable from the measuring position into the treatment position lying approximately coincident to the treatment window and vice versa, i.e. from the treatment position back into the measuring position. With such a structural measure, the probe carrying the functional element can be shifted without great effort between the different positions within the tubular housing, without additional space being claimed for the movement.

In another form of embodiment, the at least one treatment window for washing, rinsing and/or calibrating the functional element is arranged approximately directly above or below the process window, wherein the probe is mounted in a translationally movable manner, whereby the sensitive element is, via translational shifting, arranged approximately coincident with the process window or with the treatment window. The functional element can, also in the case of this embodiment, be brought easily and quickly into the desired position without additional structural changes being required for the movement of the probe.

In a variant, the probe has a round or rectangular cross section. In the case of such cross sections, translational shifting between the process window and the treatment window is possible at any time.

Alternatively, the process window and the treatment window are arranged in a plane on the end of the housing, while the functional element is secured on the end of the probe and lies, approximately parallel, relative to and opposite the housing plane, wherein the functional element is shifted by a rotary movement of the probe into positions approximately coincident with the process window or the treatment window.

Advantageously, at least two functional elements detecting the same measured variable are arranged on the probe, wherein the first functional element is arranged approximately coincident with the process window (which is open to the process medium) and the second functional element is arranged approximately coincident with the treatment window. Via the use of multiple functional elements, it is always assured that one functional element can be used for measuring in the process medium while the other functional element is being washed, rinsed or calibrated. Thus, a continuous measuring procedure can be implemented without the probe arrangement needing to be removed from the process medium for washing, rinsing or calibrating.

In an especially simple variant, the at least one treatment window is embodied as a hollow space on the inner side of the tubular housing. In such case, the hollow space is bordered on the outside by the housing and on the inside by the probe. In the case of the use of synthetic material (e.g. plastic) as probe or housing material, the immersion tube sensor can be assembled without the provision of separate seals.

In a further development, the treatment window is bordered on the inside by at least one seal. In this way, the strength of the seal of the immersion tube sensor against the process medium is improved.

Additionally, in an embodiment, at least one supply line for a treatment medium advantageously extends within the tubular housing along its lengthwise direction and opens into the hollow space of the treatment window. Due to the fact that the calibration procedure takes place within the probe arrangement, separate washing or rinsing chambers—into which the entire probe arrangement, removed from the process medium, is brought—can be omitted, whereby an especially cost-effective solution is achieved.

In a further development, the hollow space of the treatment window is connected with a line for removing the treatment medium from the hollow space, which is advantageously embodied so as to extend in the lengthwise direction of the tubular housing, especially parallel to the supply line for the treatment medium. The supply line and the line for removing the washing, rinsing and/or calibration medium can be implemented via lengthwise bores in the housing, whereby a functioning washing, rinsing or calibration system is implemented within the probe arrangement.

In an additional form of embodiment, the treatment window contains a treatment medium and is, via the probe, and in given cases other sealing elements, arranged so as to be sealed in the housing. A treatment window prefilled with treatment medium can therewith be easily positioned in the housing. This is especially advantageous, in the case of a use of the probe arrangement as a one-use article, particularly as a component of so-called "disposable" apparatuses and systems in biotechnology. Meant here by such "disposable" apparatuses and systems are non-reusable apparatuses and systems. In such case, the treatment window is advantageously filled with calibration medium. Additional structural effort for the creation of lines and openings in the housing, which serve to supply the treatment medium, can omitted.

In an especially cost-effective embodiment, the probe and/or the housing are at least partially produced from synthetic material, such as plastic.

BRIEF DESCRIPTION OF THE DRAWINGS

The invention allows for numerous forms of embodiment. Some of these will now be explained in greater detail on the basis of the appended drawing, the figures of which show as follows:

FIGS. 2a-2d show a sensor arrangement with a laterally arranged sensitive element, in the case of which a switching of the sensitive element between the measuring position and the calibration position occurs via rotation;

FIGS. 3a-3d show a sensor arrangement with a laterally arranged sensitive element, in the case of which a switching of the sensitive element between the measuring position and the calibration position occurs via translational shifting;

DETAILED DISCUSSION IN CONJUNCTION WITH THE DRAWINGS

Figure 1:
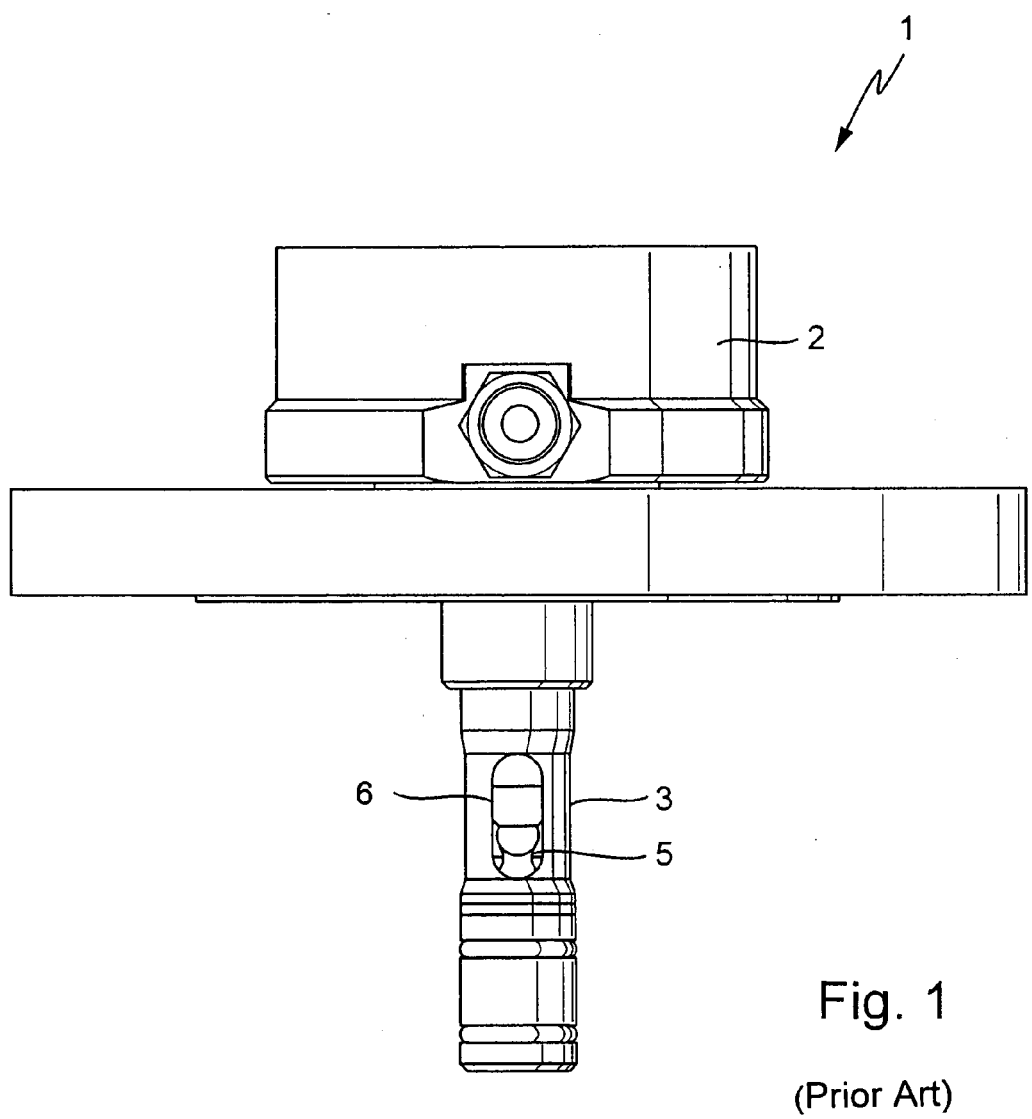
FIG. 1 is a probe arrangement according to the state of the art.

Similar features are designated with similar reference characters.

FIG. 2 shows an immersion tube sensor 1 as it is utilized for measuring process variables in liquid media. The immersion tube sensor 1 comprises, in such case, a tubular housing 2 serving as the immersion tube, whose interior contains an approximately tubular sensor 3. Arranged between housing 2 and sensor 3 is a seal 4. This seal 4 surrounds the part of the sensor 3 at which, in the lengthwise direction of the sensor, a sensitive element 5 is laterally arranged, which, in FIG. 2a, lies opposite an open process window 6. Through this process window 6, the process medium enters into the immersion tube sensor 1, and comes into contact with the sensitive element 5 when the immersion tube sensor 1 is inserted into the process medium to be measured. The sensitive element 5 can, in such case, be embodied as a pH sensor, and is arranged in a cavity 7, whose dimensions are selected in such a manner, that the sensitive element 5 approximately fits exactly into the cavity 7, and does not extend out of the cavity 7. The sensitive element 5 is connected via electrical lines (not further shown) to a control and evaluating electronics arranged outside of the immersion tube sensor 1.

Housing 2 includes an additional treatment window 8 embodied as a hollow space, which is displaced from the process window 6 by approximately 180°, and is embodied so as to be open only to the interior of the housing 2 facing the sensor 3, and is sealed outwardly by the housing 2. Treatment window 8 is connected with a first traversing bore 9, which serves as a supply line for a rinsing or calibration liquid, and ends in the upper region of the treatment window 8. This bore 9 extends along the lengthwise extent of the housing 2, and is externally filled. Parallel to the first bore 9 is a second traversing bore 10, which extends throughout the lengthwise extent of the treatment window 8 and opens at the base of the treatment window 8 into an opening 11, which connects the bore 9 with the hollow space of the treatment window 8.

In FIG. 2b, a cross section through the immersion tube sensor 1 at the height of the sensitive element 5 facing the process window 6 is presented. In such case, it is evident that the seal 4 is pressed firmly between the housing 2 and the sensor 3, in order to avoid process medium penetrating undesirably into the immersion tube sensor 1. In this way, a dead volume present in the immersion tube sensor 1 for accommodating the process medium is suppressed to the greatest extent possible. In this position, during the measurement procedure, the treatment window 8 is sealed by the sensor 3 and the seal 4.

Should the measuring procedure be interrupted and a rinsing or calibration procedure performed, the sensor 3 is rotated within the housing 2 by 180°, and the sensitive element 5 is caused to overlap with the treatment window 8, which can be seen from FIGS. 2c and 2d. In this case, the sensor body 3, pressed against the seal 4, seals the process window 6, and thus prevents a penetration of the process medium into the immersion tube sensor 1.

The seal 4 is, in such case (as can be seen as from FIGS. 2b and 2d) open opposite the process window 6 and the treatment window 8, in order to assure that either the process medium or a washing, rinsing or calibration medium reliably washes, rinses or contacts the sensitive element 5. Due to the fact that the immersion tube sensor 1 has only a very small dead volume, impurities in the interior of the immersion tube sensor 1 are minimized.

FIG. 3 shows another embodiment of an immersion tube sensor 1 having a small dead volume. In this case, the washing, rinsing or calibration procedure likewise can be performed within the immersion tube sensor 1. The immersion tube sensor 1 again includes a tubular housing 2, in which is arranged an approximately tubular sensor 3. The sensor 3, which is sealed against the housing 2 by means of the seal 4, bears on its laterally lengthwise extending surface a sensitive element 5, which is arranged in a cavity 7 of the sensor 3. The cavity 7 with the sensitive element 5 is in FIG. 3a arranged— advantageously to coincide—opposite a process window 6 in the housing 2, wherein the process window 6 in the housing 2 is embodied in a traversing manner, so that the process medium to be measured contacts the sensitive element 5, and thereby enables a measuring of the measured variable, for example, the pH value.

Approximately directly above the process window 6, a treatment window 8 extending in the direction of the lengthwise extent of the housing 2 is machined in on the inner side of the tubular housing 2, this window being outwardly sealed by the housing 2. This treatment window 8 is likewise utilized for treating the sensitive element 5, so that a lengthwise-extending bore 9 for the delivery of a treatment medium is present, this bore ending above in the hollow space of the treatment window 8. The term "treating" is meant to include, in such case, various processes such as, for example, washing, rinsing, calibrating or regenerating. It is assured that the process medium does not come into contact with the treatment medium while the process continues.

A second bore 10, which extends up to the bottom of the treatment window 8 and is connected there with the hollow space of the treatment window 8 via an opening 11, extends parallel to the first bore 9.

During the measurement procedure, the immersion tube sensor 1 is located in the position illustrated in FIGS. 3a and 3b. In such case, the second window 8 in the interior of the housing 2 is sealed by the sensor 3 and the seal 4. Should it be desired that the immersion tube sensor 1 assume its treatment position, the sensor 3 is shifted upwardly in straight line motion within the housing 2, until the sensitive element 5 overlaps with the treatment window 8, which is embodied lying above the process window 6 in the housing 2. As is evident from FIG. 3c, the seal 4 extends along the inner wall of the housing 2 and is, in such case, connected above the treatment window 8 and below the process window 6 with the housing 2 in a shape-interlocking manner. The seal 4 is, in the region of the process window 6 and in the region of the treatment window 8, open largely coincident with the cavity 7 in the sensor 3, and thus assures the contact of the process medium or of the treatment medium with the sensitive element 5. Also in the case of this embodiment of the immersion tube sensor 1, the treating of the sensitive element 5 occurs within the sensor arrangement, whereby additional calibration or washing/rinsing, chambers, which are arranged outside of the immersion tube sensor, can be omitted.

Figure 4A:
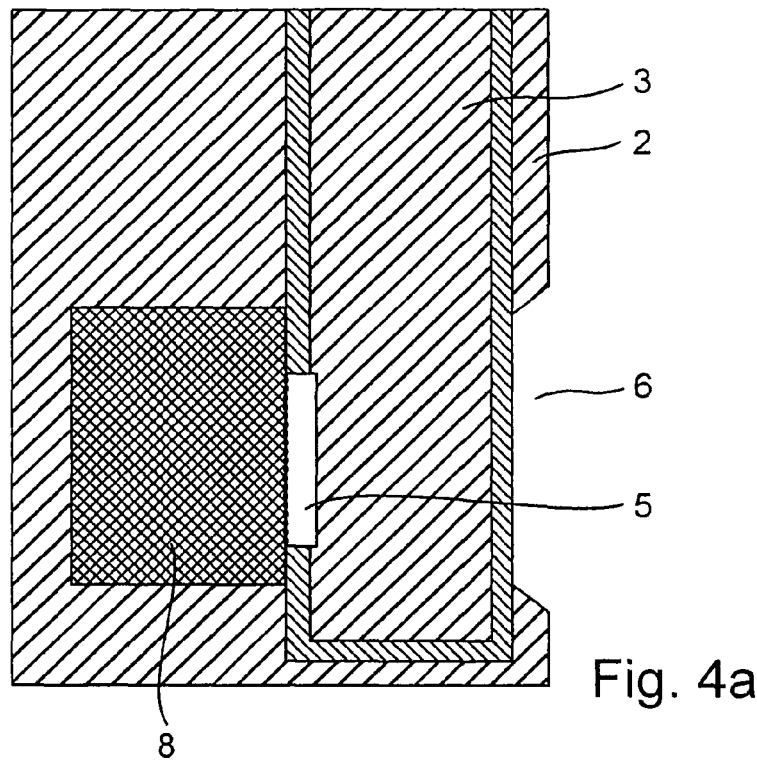
FIGS. 4a-4b show a sensor arrangement with a laterally arranged sensitive element, in the case of which a switching of the sensitive element between the measuring position and the calibration position occurs via rotation, wherein the treatment window is filled with a treatment solution.
Figure 4B:
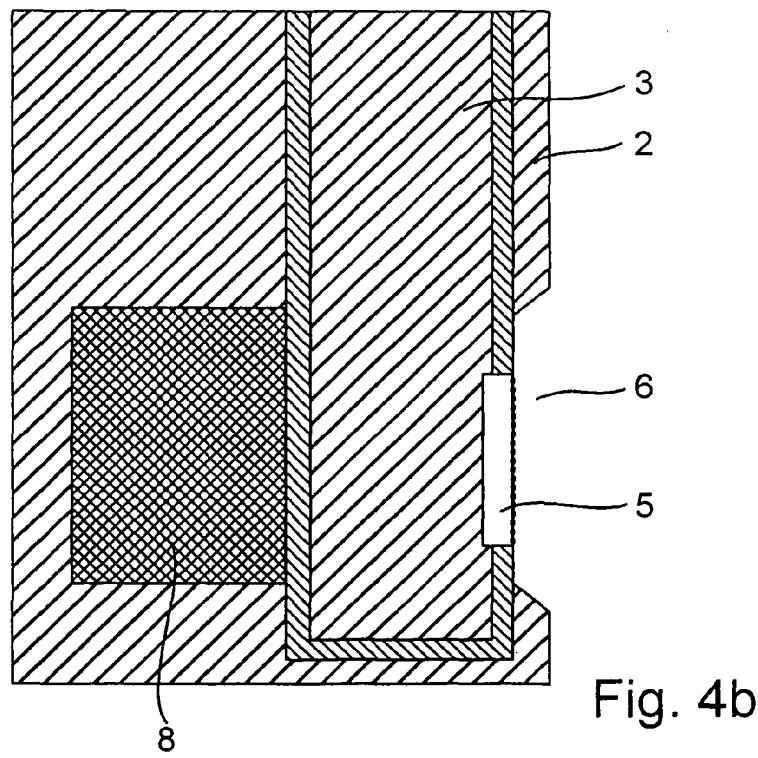

Another embodiment of the immersion tube sensor is presented in FIGS. 4 and 5. In such case, an external supplying of the immersion tube sensor 1 with a treatment medium is omitted. The treatment medium is contained in the treatment window 8, which is arranged, sealed off by the sensor 4 and, in given cases, additional sealing elements (not shown), in the housing 2. As FIG. 4a shows, during storage or during the calibration procedure, the sensitive element 5 is opposite the treatment window 8 filled with the treatment medium, wherein the extent of the treatment window 8 is dimensioned in such a manner, that its dimensions extend beyond the extent of sensitive element 5, when the sensitive element 5 is rotated into the position opposite the treatment window. The process window 6 is, in such case, sealed closed by the sensor 3, so that no process liquid can penetrate into the immersion tube sensor 1. In FIG. 4b, the immersion tube sensor 1 is shown with the laterally arranged sensitive element 5 located in the measuring position. Here, a switching of the sensitive element between the measuring position and calibration position occurs via rotation. In such case, the sensor 3 blocks the treatment window 8 filled with the treatment medium, while the sensitive element 5 lies opposite the process window 6, and, in this case, is contacted by the process medium.

Figure 5A:
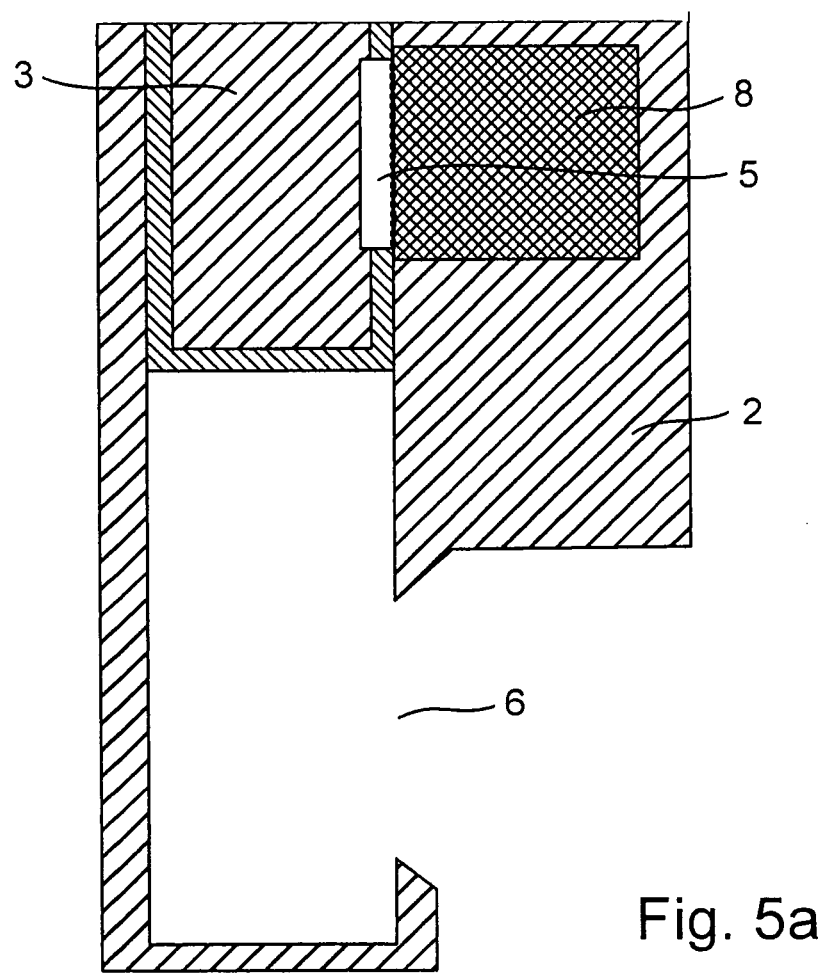
FIGS. 5a-5b show a sensor arrangement with a laterally arranged sensitive element, in the case of which a switching of the sensitive element between the measuring position and the calibration position occurs via translational shifting, wherein the treatment window is filled with a treatment solution.
Figure 5B:
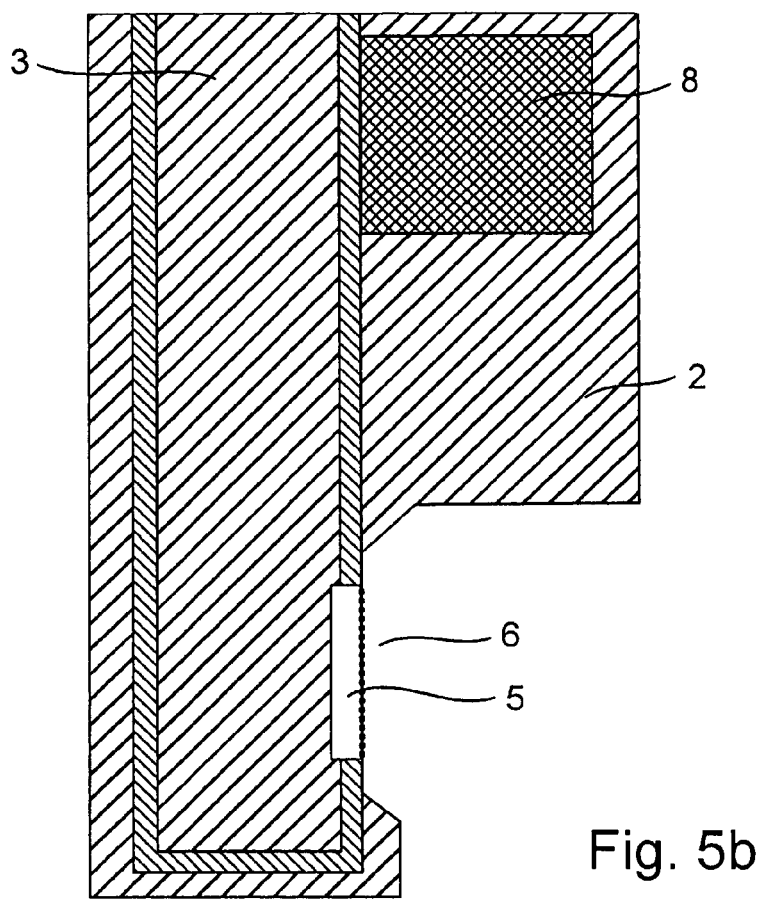

Also in the example of an embodiment, in the case of which the switching of the laterally arranged sensitive element 5 between the measuring position and calibration position occurs via translational shifting of the sensor 3, a treatment window which is filled with a treatment solution can be introduced in the housing 2 of the immersion tube sensor 1. Openings and supply lines leading to the outside can, in such case, be omitted, which simplifies the manufacture of such an immersion tube sensor 1. In FIG. 5a, the sensitive element 5 lies opposite the closed treatment window 8 filled with the treatment medium, wherein the sensitive element 5 directly faces the treatment window 8. In this position, the immersion tube sensor 1 can also be well mounted, since the sensitive element 5 is protected from the environment. FIG. 5*b* shows the sensitive element 5 in the measuring position, where it is positioned by shifting the sensor 3 from the calibration position. In the measuring position, the sensitive element 5 is contacted by the process medium in the process window 6. In the shifting variants of the immersion tube sensor 1 explained with FIGS. 3 and 5, the opportunity exists to construct the sensor 3 with a round or a rectangular cross section.

Figure 6:
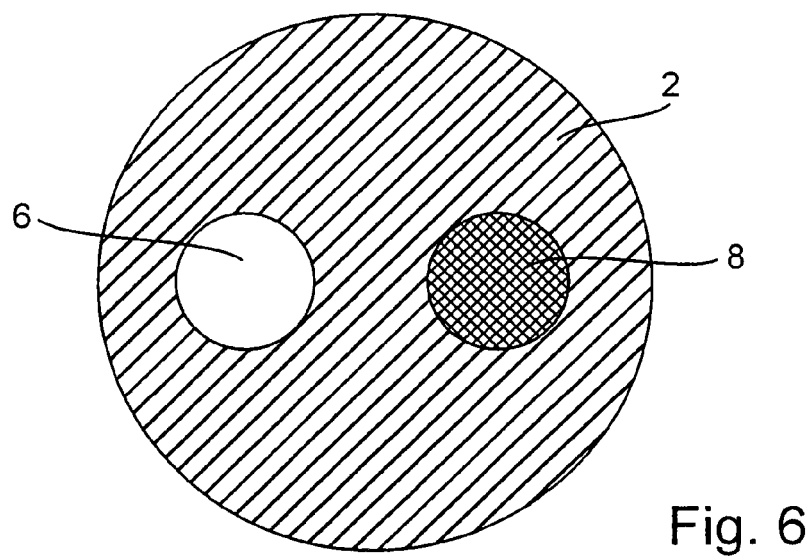
FIG. 6 shows a sensor arrangement with a sensitive element arranged in the plane of rotation, in the case of which a switching of the sensitive element between the measuring position and the calibration position occurs via a rotary movement.
Figure 7A:
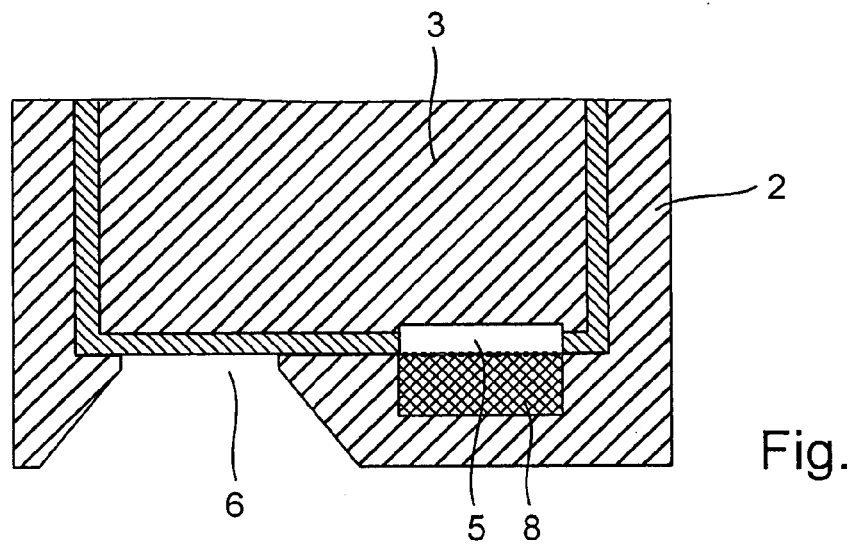
FIGS. 7a-7b show a sensor arrangement with a sensitive element arranged in the plane of rotation, in the case of which a switching of the sensitive element between the measuring position and the calibration position occurs via a rotary movement, wherein the treatment window is filled with a treatment solution.
Figure 7B:
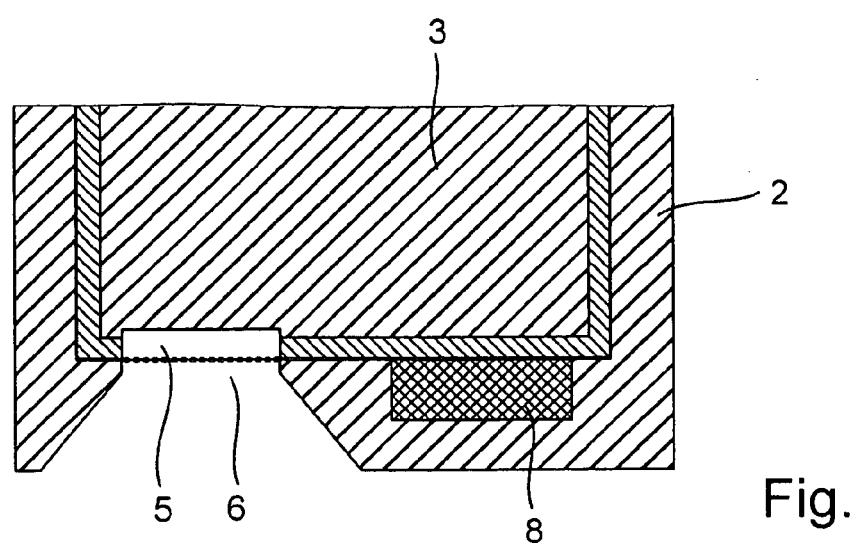

In FIG. 6, another embodiment of the immersion tube sensor 1 is presented. In the case of this so-called "revolver variant", the housing 2 of the immersion tube sensor 1 is closed on the end—except for the process window 6, which lets in the process medium—and is immersed in the process medium. In addition to the process window 6, the treatment window 8 is also arranged in the plane of rotation of the immersion tube sensor 1. The treatment window 8 is, in this example, also sealed off and contains the treatment medium. The sensitive element 5 is arranged on the end of the sensor 3 and faces the treatment window 8, which is machined into the housing 2, while the process window 6 is sealed by the sensor 3 and, in given cases, additional sealing elements (not shown) (FIG. 7*a*). In the case of a highly accurate matching of the sensor 3 to the housing 2, a seal 4 can be omitted. In FIG. 7*b*, the "revolver variant" is shown in the measuring position. In such case, the sensitive element 5 lies opposite the process window 6, wherein it is contacted by the process medium. From the storage position or calibration position, the sensitive element is transferred via rotation of the sensor 3 about its longitudinal axis into the measuring position.

The immersion tube sensor 1 shown can be used both in screw-in assemblies, in the case of which the sensor only can be replaced when the process is interrupted and no process medium is contacting the sensor, as well as also in retractable assemblies, where the process continues during the replacing of the immersion tube sensor 1. The material of the probe 3 and/or of the housing 2 is preferably a synthetic material (such as plastic), glass, metal or ceramic. The probe 3 and/or housing 2 can also be embodied without a seal 4.

The described solution of the invention is also applicable in biotechnology in the case of sterile, non-reusable systems, in the case of which the sensors, for example, are inserted in a non-reusable reactor, and remain there for a longer period of time, up to their start-up. In the case of this application, probe 3 and/or housing 2 are composed of gamma sterilizable materials, preferably synthetic material. Storage of the sensor 3 with the sensitive element 5 occurs, in such case, in contact with the treatment solution, whereby a higher long-term stability is achieved. In this way, for example, in the case of potentiometric pH sensors, a drying out of the glass membrane is reliably prevented. A running out of the reference half-cell can also effectively be prevented with the assistance of the described probe arrangement. The treatment solution can be used for calibrating and/or adjusting the sensor both during start-up as well as also further thereafter. The treatment solution is only discharged from the treatment window to a small degree. Via the proposed construction, a mechanical stabilizing of the sensor 3 and of the sensitive element 5 occurs, whereby danger of fracture is limited.

The invention claimed is:

1. A probe arrangement, comprising:
a probe; and
a tubular housing, with said probe being arranged within said tubular housing, wherein:
said tubular housing has at least one process window open to a process medium;
at least one functional element is arranged on said probe, which is surrounded by the process medium;
said tubular housing has at least one treatment window lying opposite said probe, for washing, rinsing and/or calibrating said at least one functional element;
said at least one functional element is movable between said at least one process window and said at least one treatment window, and, during measuring in the process medium, said at least one functional element is arranged approximately coincident with said at least one process window;
said at least one functional element is arranged on said probe to extend laterally of said probe, and in the length direction of said tubular housing;
said at least one treatment window is advantageously arranged opposite said at least one process window at an approximately an equal height; and
said probe is mounted rotatably, whereby said at least one functional element is rotatable from a measuring position into a treatment position lying approximately coincident with said at least one treatment window and vice versa, from the treatment position back into the measuring position.

2. The probe arrangement as claimed in claim 1, wherein:
said at least one functional element is secured on said probe.

3. The probe arrangement as claimed in claim 1, wherein:
said at least one functional element is arranged in a cavity of said probe.

4. The probe arrangement as claimed in claim 1, wherein:
said at least one treatment window for washing, rinsing and/or calibrating said functional element is arranged approximately directly above or below said process window;
said probe is mounted in a translationally movable manner, whereby said functional element is, via translational shifting, arranged approximately coincident with said process window or with said treatment window.

5. The probe arrangement as claimed in claim 4, wherein:
said probe has a round or rectangular cross section.

6. The probe arrangement as claimed in claim 1, wherein:
at least two functional elements, which detect the same measured variable, are arranged on said probe;
the first functional element is arranged approximately coincident with said process window open to the process medium, and the second functional element is arranged approximately coincident with said treatment window.

7. The probe arrangement as claimed in claim 1, wherein:
said probe and/or said housing are produced at least partially from synthetic material.

8. A probe arrangement, comprising:
a probe; and
a tubular housing, with said probe being arranged within said tubular housing, wherein:
said tubular housing has at least one process window open to a process medium;
at least one functional element is secured on said probe, which is surrounded by the process medium;
said tubular housing has at least one treatment window lying opposite said probe, for washing, rinsing and/or calibrating said at least one functional element;
said at least one functional element is movable between said at least one process window and said at least one treatment window, and, during measuring in the process medium, said at least one functional element is arranged approximately coincident with said at least one process window of said housing;

said at least one process window and said at least one treatment window are arranged in a plane on an end of said tubular housing, while said at least one functional element is secured on an end of said probe and lies approximately parallel to and opposite said housing plane; and said at least one functional element is arranged via a rotary movement of said probe approximately coincident with said at least one process window or with said at least one treatment window.

9. A probe arrangement, comprising:

a probe; and a tubular housing, with said probe being arranged with said tubular housing, wherein:

said tubular housing has at least one process window open to a process medium;

at least one functional element is secured on said probe, which is surrounded by the process medium;

said tubular housing has at least one treatment window lying opposite said probe, for washing, rinsing and/or calibrating said at least one functional element, said at least one functional element is movable between said at least one process window and said at least one treatment window, and, during measuring in the process medium, said at least one functional element is arranged approximately coincident with said at least one process window of said housing;

said at least one process window and said at least one treatment window are arranged in a plane on an end of said tubular housing, while said at least one functional element is secured on an end of said probe and lies approximately parallel to and opposite said housing plane; and said at least one functional element is arranged via a rotary movement of said probe approximately coincident with said at least one process window or with said at least one treatment window.

10. The probe arrangement as claimed in claim 9, wherein:

said treatment window is bordered on an inner side by at least one seal.

11. The probe arrangement as claimed in claim 9, wherein:

the hollow space of said treatment window is connected with a line for removing a treatment medium from said hollow space, which is advantageously embodied so as to extend within the lengthwise direction of said tubular housing, parallel to the at least one supply line for the treatment medium.

12. The probe arrangement as claimed in claim 9, wherein:

said treatment window contains a treatment medium, and is arranged so as to be sealed off in said housing.

\* \* \* \* \*